United States Patent [19]

Hauser

[11] Patent Number: 5,429,602
[45] Date of Patent: Jul. 4, 1995

[54] PROGRAMMABLE PORTABLE INFUSION PUMP SYSTEM

[76] Inventor: Jean-Luc Hauser, 1499 Chemin S. Maymes, F-06600 Antibes, France

[21] Appl. No.: 170,208
[22] PCT Filed: Apr. 28, 1993
[86] PCT No.: PCT/FR93/00414
§ 371 Date: Jun. 10, 1994
§ 102(e) Date: Jun. 10, 1994
[87] PCT Pub. No.: WO93/21978
PCT Pub. Date: Nov. 11, 1993

[30] Foreign Application Priority Data

Apr. 29, 1992 [FR] France .................. 92 05310

[51] Int. Cl.[6] ............................................ A61M 31/00
[52] U.S. Cl. ............................................... 604/65
[58] Field of Search .............. 128/DIG. 12, DIG. 13; 604/30, 31, 65-67, 118, 151, 246

[56] References Cited

U.S. PATENT DOCUMENTS

| | | |
|---|---|---|
| 4,270,532 | 6/1981 | Franetzki et al. . |
| 4,624,661 | 11/1986 | Arimond .................. 604/151 |
| 4,676,776 | 6/1987 | Howson . |
| 4,756,706 | 7/1988 | Kerns et al. . |
| 4,810,243 | 3/1989 | Howson . |
| 5,010,473 | 4/1991 | Jacobs ...................... 604/65 X |
| 5,088,981 | 2/1992 | Howson et al. . |
| 5,116,312 | 5/1992 | Blankenship et al. ..... 604/65 X |
| 5,170,817 | 12/1992 | Sunderland .......... 128/DIG. 12 X |
| 5,181,910 | 1/1993 | Scanlon .................... 604/65 X |
| 5,211,626 | 5/1993 | Frank et al. ............... 604/65 |
| 5,317,506 | 5/1994 | Coutré et al. ............. 604/65 X |

FOREIGN PATENT DOCUMENTS

| | | |
|---|---|---|
| 0002775 | 7/1979 | European Pat. Off. . |
| 8400493 | 7/1983 | WIPO . |

Primary Examiner—C. Fred Rosenbaum
Assistant Examiner—Frank Wilkens, III
Attorney, Agent, or Firm—Francis A. Sirr; Earl C. Hancock

[57] ABSTRACT

A portable and programmable infusion pump system is disclosed for injecting one or more medicinal substances into an individual under the control of the individual. A common controller unit and microprocessor is provided for one or more pump units. Each pump unit includes a chamber for holding a medicinal substance, an infusion tube that is connected to the chamber and is adapted to be connected to the individual, and a motor driven pump for pumping the medicinal substance through the infusion tube. The individual programs the microprocessor to perform one or more infusion processes by use of a keyboard, a card reader, a bar code reader, or a modem. Each motor and pump are controlled in accordance with its program parameters as contained in the programmed microprocessor. A pressure sensor and an air bubble detector is associated with each infusion tube, and these sensors and detectors are connected to the microprocessor.

27 Claims, 8 Drawing Sheets

PROGRAMMABLE PORTABLE INFUSION PUMP SYSTEM

BACKGROUND OF THE INVENTION

1. Field of the Invention

The present invention relates to a programmable portable infusion pump system for automatically injecting a medicinal substance into a patient, of the type comprising a supply chamber containing the medicinal substance, a pump unit comprising a motor and a pump driven by the motor to inject the medicinal substance into an infusion tube connected to the patient's body, and a programmable controller enabling the motor at instants programmed in advance.

2. Description of Prior Art

It has become more and more common to treat certain diseases by regular intravenous, intra-arterial or intra-rachidian injecting of a medicinal substance. In order to leave the patient with some autonomy and not force him to spend too frequent of stays in hospitals and get the infusions performed on him, portable systems have been realized.

An infusion tube is then available connected to the patient's body so as to perform the infusion when necessary. When the infusion is to be performed, a portable infusion pump system that the patient carries is connected to the infusion needle. Infusion is performed by a pump driven by a motor, the latter pump injecting the medicinal substance coming from a supply chamber into the patient's body thru the infusion tube. The motor, the pump and the supply chamber are integrated in the portable infusion pump system.

Programmable portable infusion pump systems have been realized. In such systems, a controller integrated in the system allows to program the therapeutic protocol i.e. the metering of the infusion to be performed, its duration, and the time when it needs be started. Current systems of this type comprise to this effect a controller which is indeed a simple programming means in that it allows programming of the therapeutic protocol relative to the instant when the system is turned on, but does not allow a programming according to solar time. Besides, programming is usually done thru multifunction keys, which results in limiting the programming possibilities in case there are few keys, or increases possibilities of mistakes in case there are too many functions.

In the majority of current systems, only the supply chamber containing the medicinal substance, also called 'cassette', is removable from the whole system, so as to allow its replacement when it is empty. On the contrary, the pump unit and the controller are made one element, which is a major drawback of the current programmable infusion pump systems.

There also exists programmable portable systems such as the insulin infusion system described in U.S. Pat. No. 4,270,532 in which a unit containing the motor, the pump and the insulin supply chamber is removable from the controller. But this system features two main drawbacks. Indeed it is more and more common to inject several medicinal substances simultaneously to improve the efficiency of a therapeutic treatment. In this case, the patient needs then to get a second portable infusion pump system to allow two simultaneous infusions but still keeping his autonomy without being confined in hospitals. The cost of two portable infusion pump systems becomes then prohibitive, not to mention the difficulty for the patient to carry two infusion pump systems which, even though not heavy, are cumbersome. The second drawback of this system is that the controller becomes autonomous only after having been programmed by an external programming means connected to the controller. This programming therefore requires the patient to go to the hospital where the programming means may be found each time an infusion is required.

SUMMARY OF THE INVENTION

The goal of the present invention is therefore to allow two or more simultaneous and ambulatory infusions using a simple, not cumbersome and lowcost system.

Another goal of the invention is to provide a programmable portable infusion pump system requiring only one controller to allow several simultaneous infusions.

Still another goal of the invention is to provide a programmable portable infusion pump system in which the programming is performed directly with the patient thanks to a controller programmable without any external programming means.

The object of the invention is then a programmable portable infusion pump system in which the controller includes a microprocessor, a keyboard and a screen, the microprocessor being directly programmed thru the keyboard to command the motor according to a predetermined infusion program and providing information regarding the infusion process thru displaying on the screen.

Another object of the invention is a programmable portable infusion pump system of the type recited above also comprising at least a second system including a pump-unit and a supply chamber, connected to the controller, the second system being detachable from the controller but with the second pump-unit still being controlled by it, so that the controller can control several simultaneous infusions.

In summary, the programmable pump system according to the invention is characterized by a high modularity and complete autonomy allowing the patient equipped with it to not depend on hospitals or not be encumbered in his everyday life.

BRIEF DESCRIPTION

Goals, objects and characteristics of the invention will be better understood from the following description read in conjunction with the schematics in which:

FIG. 1 represents one embodiment of the programmable portable infusion pump system according to the invention, FIG. 2 represents the portable infusion pump system of FIG. 1 with the pump-unit detached from the controller, FIG. 3 represents an embodiment of the invention comprising only one controller used for controlling an attached pump-unit and a detached pump-unit, FIG. 4 represents an embodiment of the device assembling the cassette with the pump-unit, FIG. 4a is a side view of the clip used as an assembling device of the cassette with the pump-unit as illustrated in FIG. 4, FIG. 4b represents the assembling device of FIG. 4a when in the open position, FIG. 5 is a synoptic diagram representing the different elements of the programmable system according to the invention and their interconnections, FIG. 6 is an algorithm showing the process steps to configuring the programmable system according to the invention, FIG. 7 is an algorithm showing the process steps to programming the programmable system according to the invention, FIG. 8 is an algorithm showing the process steps to starting up the programmable system according to the invention, FIG. 9 is an algorithm showing the simultaneous functioning of the two pump-units incorporated into the programmable infusion system according to the preferred embodiment of the invention, FIGS. 10a-10d represent the controller of the programmable system according to the invention at the different steps in the programming process.

DESCRIPTION OF THE PREFERRED EMBODIMENTS

Figure 1:
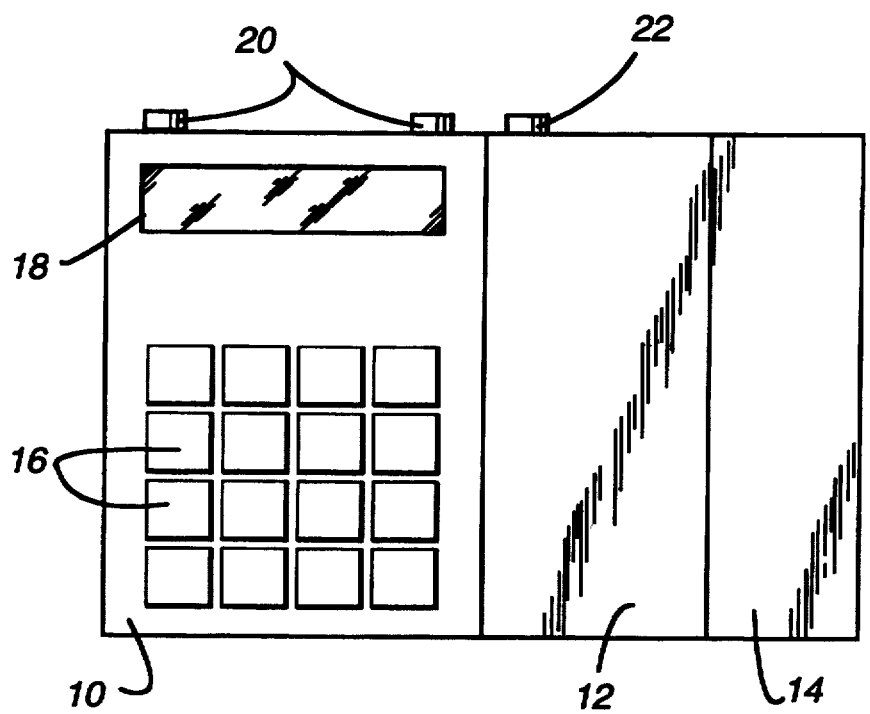

As illustrated in FIG. 1, the programmable portable infusion pump system in a preferred embodiment comprises a controller 10, a pump-unit 12 and a supply chamber 14, all in a single, compact piece, which can be easily carried by the patient. The controller comprises a keyboard 16 designed for inputting commands and in particular the parameters which allow to define the therapeutic protocol, and a screen 18, preferably a Liquid Crystal Display to allow displaying certain parameters or control results of the infusion. This controller can be implemented with an advanced microprocessor specifically adapted to provide adequate Input/Outputs. The controller also features two pins 20 used for remote control of the detached pump-unit and supply chamber together. The controller has batteries for powering the whole system, a processing unit, a Read Only Memory and READ/WRITE memory.

The pump-unit 12 comprises elements identical to those of the prior art systems, i.e. an electrical motor commanded by the controller, a pump of the peristaltic type or any other equivalent type, an electronic circuit connected to the controller, and the portion of an infusion tube from the supply chamber 14 which under the activation of the pump injects the medicinal substance into the patient's body. Finally, the pump-unit comprises a pin 22 aimed at being connected to the controller when the pump-unit is detached from the controller 10.

Figure 2:
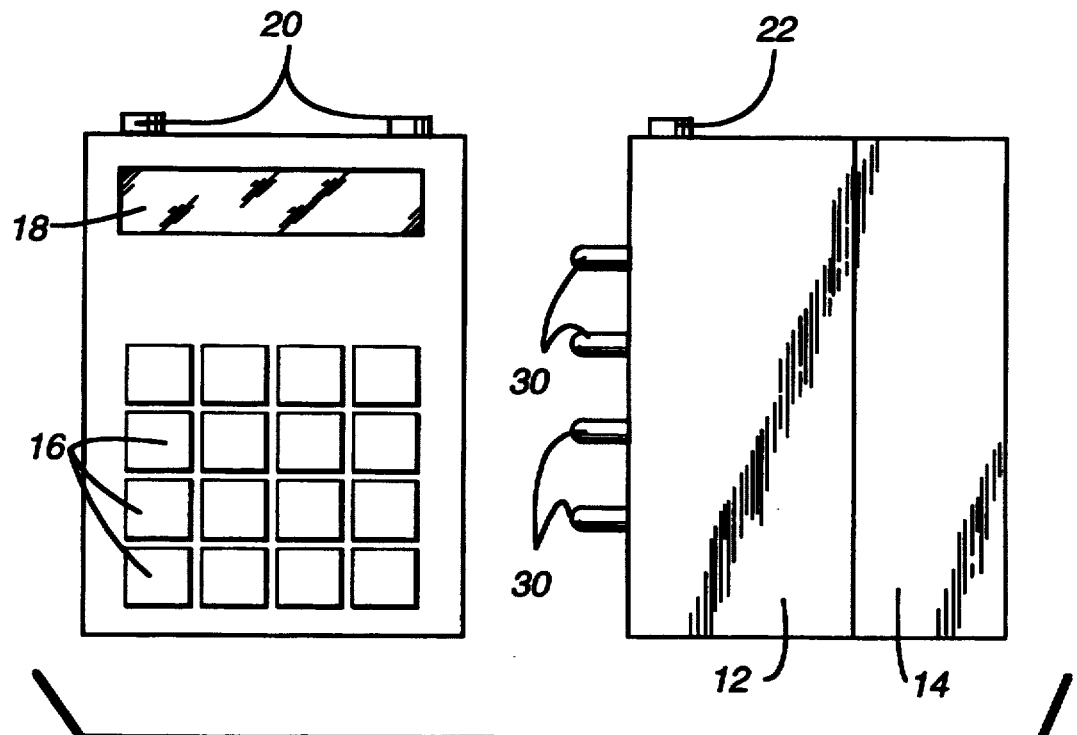

The supply chamber 14 is generally constituted by a throw-away cassette comprising a flexible bag made of polymer containing the medicinal substance enclosed in a rigid casing. FIG. 2 represents the pump-unit together with the cassette detached from the controller. A group of 4 pins 30 allows the pump-unit 12 to be connected and attached to the controller. But pins 30, on top of their mechanical function, also ensure the electrical connection between the controller and the pump-unit when the latter is not detached. It will be obvious that the function of pins 30 could be only an electrical connection, the mechanical attaching being then realized thru well-known means. When the pump-unit is detached, either the pins are protected by a cover, or their design is such that they can be retracted within the pump-unit by pushing them therein after a quarter round rotation.

Although on FIGS. 1 and 2, only one pump-unit (and the associated cassette) is represented, it is possible to have another pump-unit (and the associated cassette) attached to the other side of the controller. It is one of the advantages of the invention that the controller can simultaneously command two pump-units when two infusions of different medicinal substances are to be performed simultaneously. Thus, the second pump-unit would be attached to the left side of the controller by a group of pins identical to the pins 30 illustrated in FIG. 2.

Figure 3:
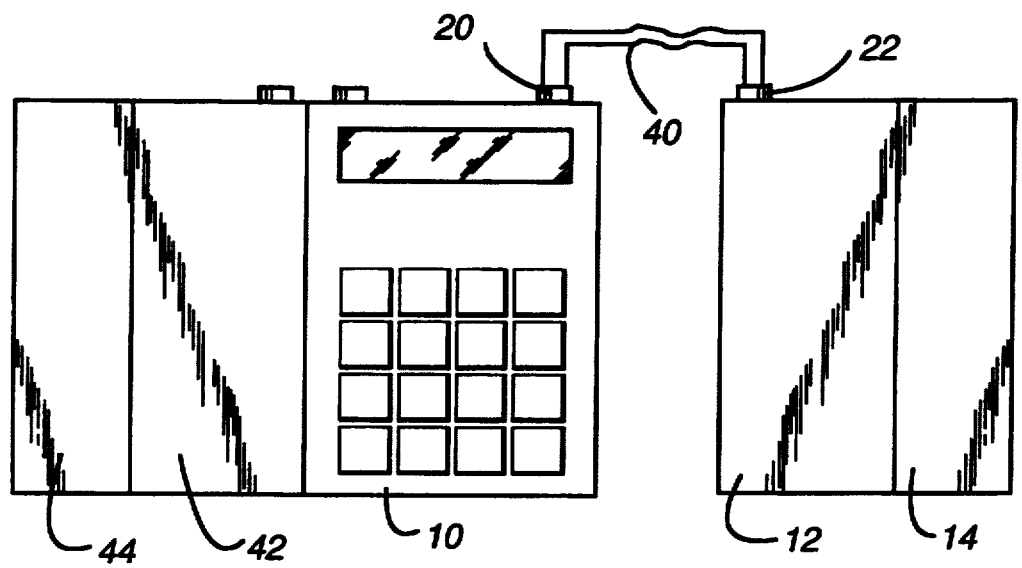

The commanding by the controller of two simultaneous infusions can be achieved in a different fashion, as will be seen with respect to FIG. 3. As illustrated, the pump-unit 12 and the associated supply chamber 14 have been detached from the controller 10. However, there is an electrical connection 40 between the controller 10 and the pump-unit 12 respectively thru pins 20 and 22, that allows the pump-unit to remain under the command of the controller and yet be carried at different points on the patient's body. At the same time the controller 10 keeps commanding an infusion performed with the pump-unit 12, the same controller 10 keeps commanding a second pump-unit 42 and the associated supply chamber 44 which are attached directly to the controller 10.

One can then see that, in the preferred embodiment of the invention, the controller can also command four simultaneous infusions, by using two pump-units directly attached to the controller, and two other pump-units remotely connected thru pins 20 of the controller. It will be obvious that the number of pump-units being under the command of the controller has no limit but the one limit set by the capability of performing simultaneous infusions.

Figure 4:
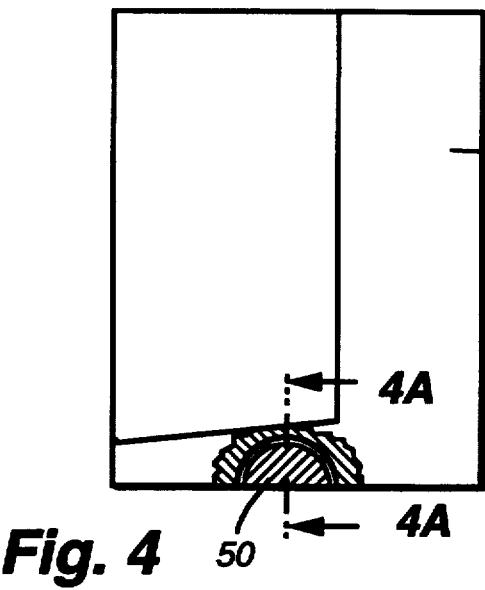
Figure 4A:
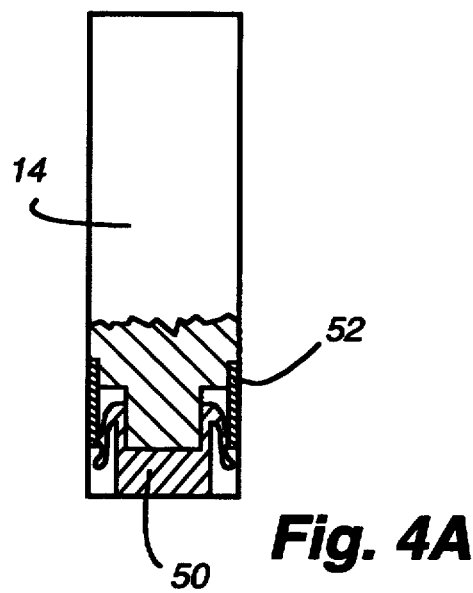
Figure 4B:
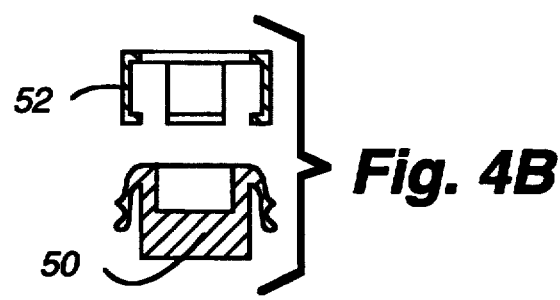

The removable link between the pump-unit and the supply chamber can be realized in an embodiment illustrated on FIGS. 4 and 4a using an elastic clipping mechanism. On FIG. 4 it can be seen that the supply chamber features a horizontal part having a clip 50 which allows to lock the supply chamber or cassette on the pump-unit. FIG. 4a illustrates the locking clip 50 following section A, when in the closed and open positions, and shows how two square parts 52 on the pump-unit cooperate with two shoulders on clip 50 of the supply chamber to interlock. This particular locking system can as is well-known be replaced by any other locking system without it being out of the scope of the invention.

Figure 5:
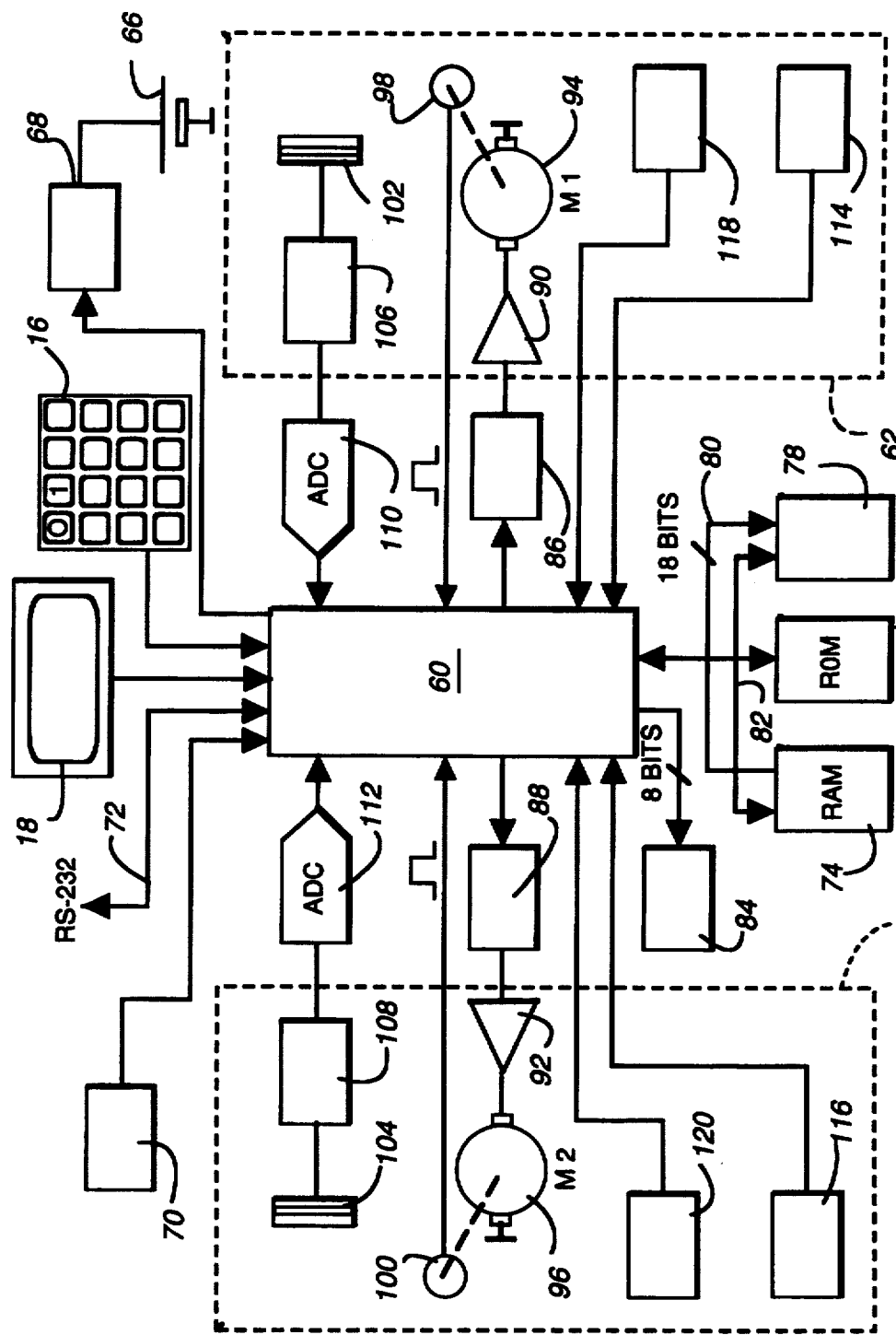

FIG. 5 is a synoptic diagram representing the different elements of a system comprising two pump-units and their interconnections.

The overall representation comprises a microprocessor or microcontroller which makes up the controller processing unit connected to all of the elements and in particular to the two pump-units 62 and 64. The microprocessor has its own power source 66 (comprising batteries) which is connected thru a voltage monitoring circuit 68. The monitoring circuit 68 features a watchdog so as to interrupt microprocessor 60 in case of failure of the power source 66. Programming of the controller is performed mainly thru keyboard 16, but can also be performed thru other known means. Thus programming can be performed thru bar code reading and an optical pen that a doctor or nurse can use to input the command process of a particular infusion. Or, it is equally possible to perform programming of the controller thanks to an electronic card that one needs to introduce in the controller or a peripheral connected to it, to immediately input the desired command process. The preferred embodiment comprises a reading system of bar code 70 as represented on FIG. 5.

The controller can also be connected to a personal computer via an RS-232 type connection 72. Such a connection will also allow to program the controller using the computer instead of the keyboard, and also to store data from the controller memory for statistics purpose. The same connection can be used too with a modem. In that case it will be easy for the patient to connect his controller to the telephone network so that a doctor also equipped with a modem can remotely monitor the good performance of the therapeutic treatment, or even proceeds with the programming of the controller by instructions transmitted thru the telephone line.

Finally, the controller could also be equipped with a radio receiver and remotely be programmed with an associated emitter, in which case a code is necessary for such a programming to take place.

Displaying of the data collected in the course of the infusion, or input by the doctor programming thru keyboard 16 or code bar reader 70 is performed at the screen 18 which is preferably a liquid crystal display of 4 lines of 16 characters.

The controller features a Random Access Memory (RAM) 74 of 512 kilo-bytes capacity for storing data input at the keyboard and data about the ongoing infusion, a Read Only Memory (ROM) 76 where reside instructions of the program commanding operations of the system, also of a capacity of 512 kilo-bytes, which is preferably of the EPROM type, i.e. which is electrically erasable and re-programmable so that the program commanding operations can easily be updated. The controller obviously features a real time clock 78 mandatory for allowing chronotherapy i.e. program the infusions (in particular the substance flow and its evolution) relative to absolute time, and not to predetermined time intervals relative to the system power-on. RAM 74, ROM 76 and real time clock 78 are addressed by microprocessor 60 thru a 16-bit address bus 80, and data exchange between those three entities is done thru an 8-bit data bus 82.

An alarm system or 'beep' 84 can be connected to microprocessor 60 so as to emit a sound at any interrupt or failure of the system when there is an ongoing infusion.

Each one of the two pump-units 62 or 64 is connected to the microprocessor 60 via a command circuit 86 or 88 with associated watchdog, which transforms instructions of the controller 60 into electrical command signals, and an amplifier 90 or 92. Each one of the motors 94 (M1) or 96 (M2) features a magnetic encoder 98 or 100 transmitting to microprocessor 60 synchronizing signal for speed regulation purposes.

The part of the infusion tube which is inside the pump-unit is equipped with a pressure sensor 102 or 104 in charge of inputting to microprocessor 60 the measuring of pressure within the portion of the infusion tube under pressure from the pump, after rectifying the signal thru the circuit 106 or 108 and conversion from analog to digital with the converter (ADC) 110 or 112.

The latter portion of the infusion tube which is inside the pump-unit is also equipped with an air bubble detector 114 or 116 being able to signal to the controller in case air bubbles have entered the infusion tube.

Finally, each pump-unit 62 or 64 features means for detecting the presence of a cassette or pump-unit 118 or 120 and automatically signal the microprocessor 60 in case of pump-unit connection to the controller or cassette installation.

Such a system of portable infusion pump system has numerous advantages over prior art technique. The controller can thus be programmed for chronotherapy, as seen above. This possibility allows to adapt the infusion to the patient's biological pace. Also the controller has a memory (RAM) where data about the patient are stored. One can thus program the therapeutic protocol taking into account certain control parameter values not to be exceeded during the infusion. It is also possible to connect the controller to sensors placed in or on the patient's body and which transmit to the controller physiological data allowing said controller to program the infusion parameters according to the received physiological data. The memory also allows storing all data, being results or incidents if any during the infusion, and thus knowing the history of the performed therapy.

The various procedures allowed with the system according to the invention are now going to be described with respect to FIGS. 6 to 9.

Figure 6:
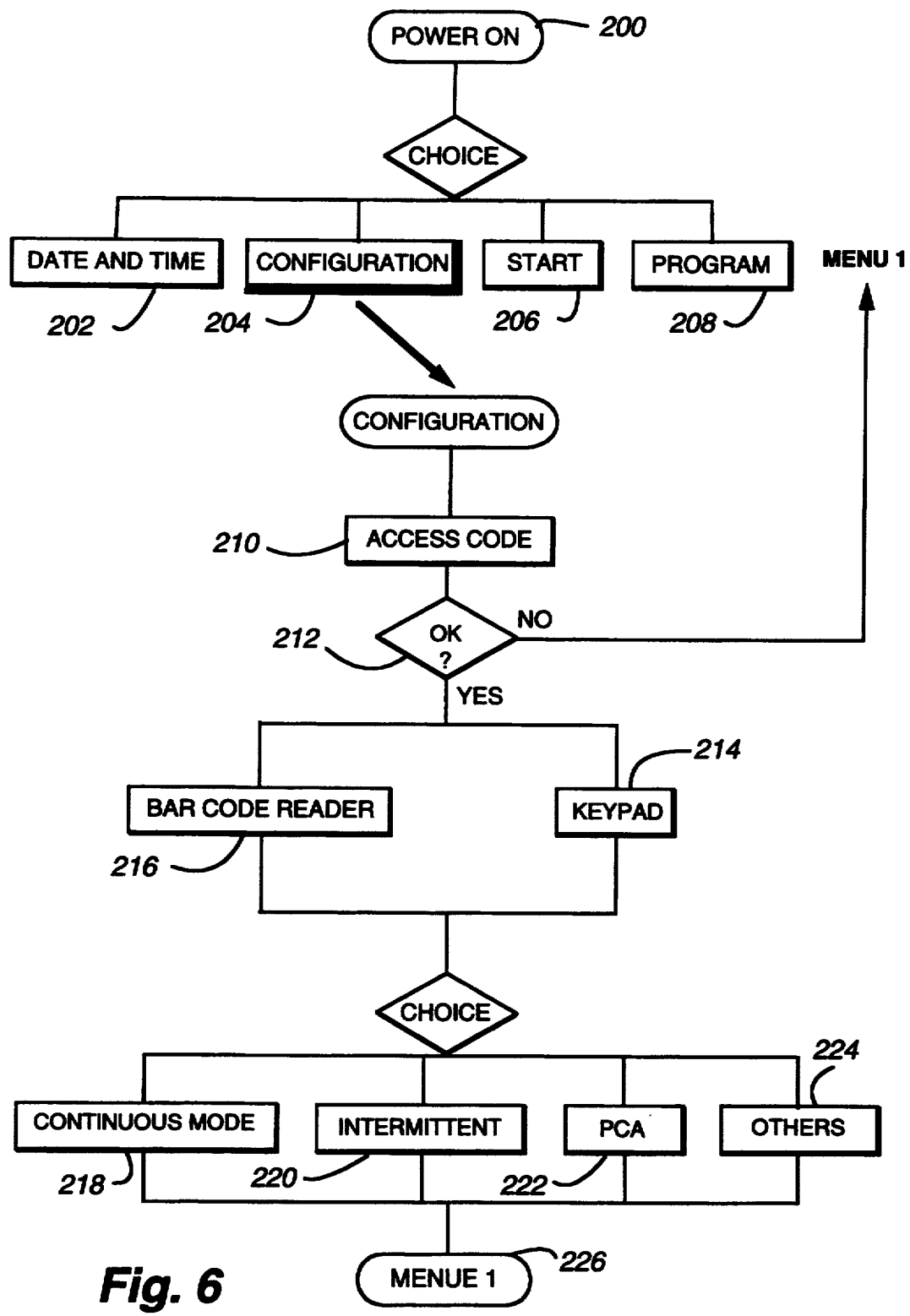

As illustrated FIG. 6, after power-on (200), a menu is presented to the user for various possible procedures displayed on the screen 18 of the controller: DATE AND TIME (202), CONFIGURATION (204), START (206) and PROGRAM (208).

Procedure DATE AND TIME, although mandatory since it allows real time programming of the controller, is of no interest and will not be described in details.

One of the essential characteristics of the portable programmable infusion pump system according to the invention is to be programmable by a doctor or other specialist when the system is on a patient, but also to facilitate its usage by the medical personnel. It is thus arranged to configure the system in a particular functioning mode prior to any programming. User interface is therefore greatly simplified and using of the system is much more userfriendly.

Procedure CONFIGURATION is thus chosen using a cursor moved on the screen with keys of the keyboard. The screen then displays 'access code' (210) to prompt the user to input its access code. If an incorrect access code is input, the user is directed (212) to menu 1 and names of the accessible procedures are once more displayed. If the access code is correct, choice is given to input the configuration either thru the keyboard (214) or the bar code reader (216). After that, the screen displays all possible modes: CONTINUOUS MODE (218), PCA (222) and others (224). PCA mode (Patient Control Analgesia) is a pain relief mode performed with morphine or other analgesic substance.

Finally, after data corresponding to a specific configuration mode are input, the system returns to menu 1 (226).

Once the system is configured in one mode, the application will prompt only the latter configuration mode until another configuration is input in the system. The advantage of this procedure is that it allows modifying when needed a whole group of systems. Subsequent programming operations are reduced to a minimum which greatly improves usage.

Figure 7:
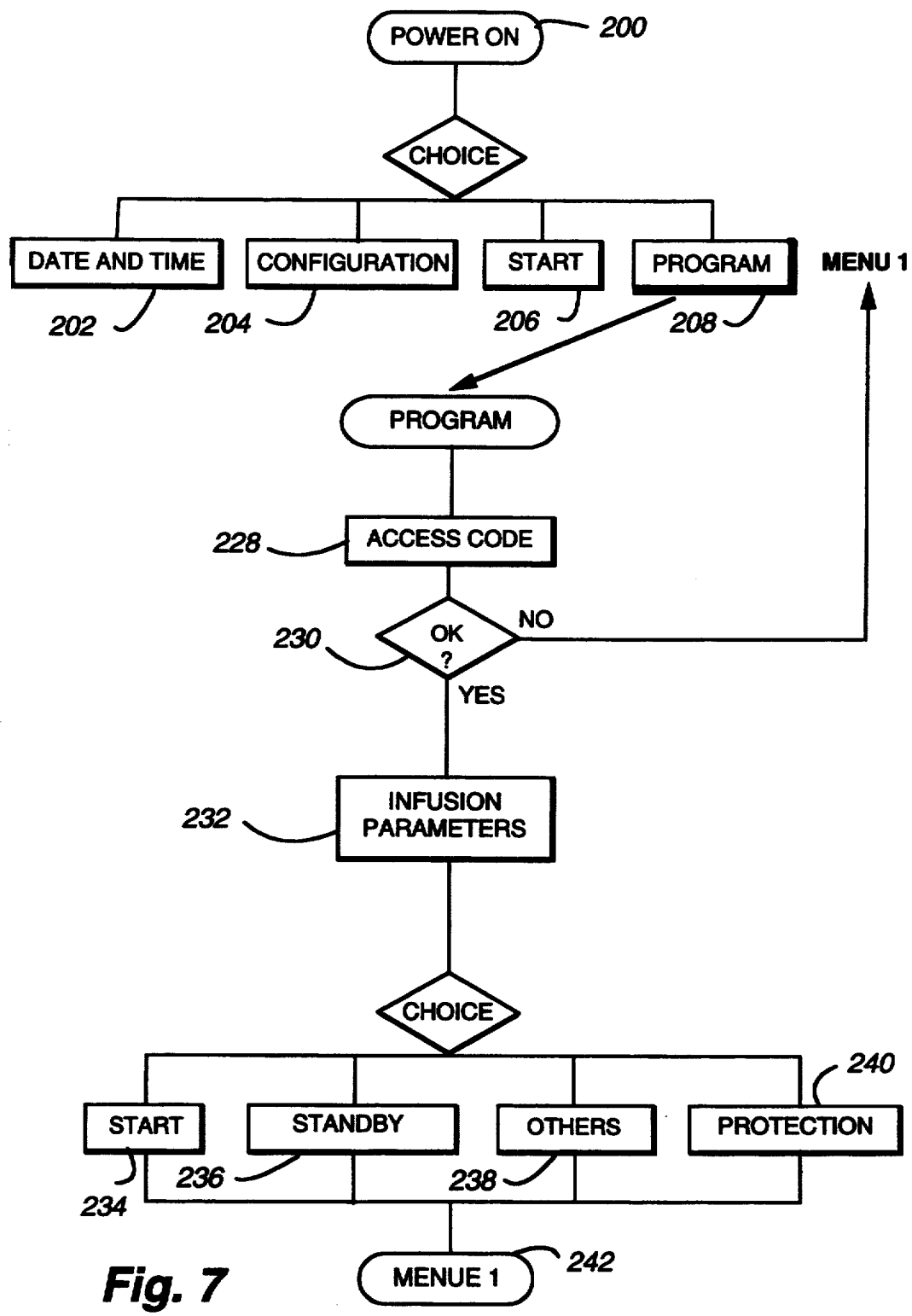

After system configuration, the pump can be programmed for an infusion as illustrated FIG. 7.

When the PROGRAM procedure has been chosen (208) in menu 1, the screen prompts for the access code (228). If an incorrect access code is input, decision (230) is taken to return to menu 1. If the correct access code is input, the controller displays the various infusion parameters to be input thru keyboard (232). After the infusion parameters have been input, a menu is proposed to the user with START of the infusion (234), STANDBY (236), OTHERS (238) and protection (240). Those functions will be explained in further detailed below.

When programming is over, return is made (242) to menu 1 as previously.

Figure 8:
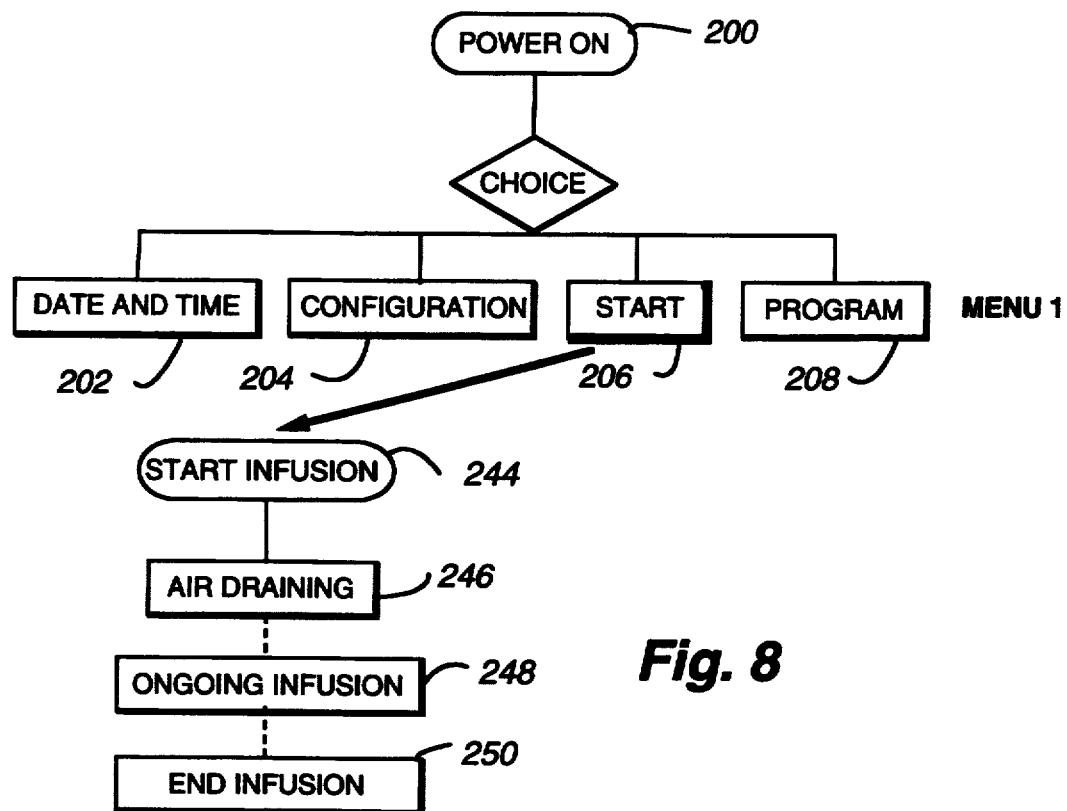

FIG. 8 illustrates the procedure for starting (206) an infusion. After triggering the beginning of the infusion (244), it is proceeded with the draining (246) of any air from the infusion tube. Then infusion is performed (248) with possible display of infusion data on the controller screen. Infusion is ended by an indication of the end (250) displayed on the screen.

When the system features two pump-units as is the case in the preferred embodiment of the invention, pressing a specific key of the keyboard allows accessing the resources of the second pump-unit. The second infusion pump can then be configured, programmed, the infusion can be started, all independently of the first pump.

Figure 9:
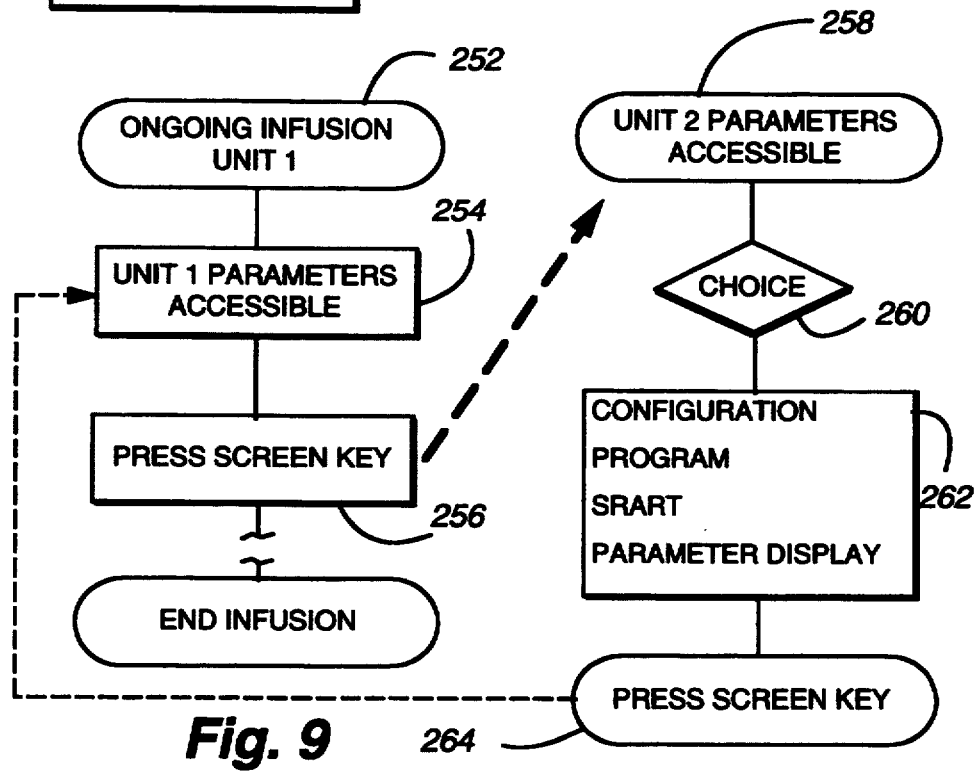

Simultaneous functioning of the two pump-units is illustrated in FIG. 9. Supposing there is an ongoing infusion (252) on unit 1 or first pump-unit, infusion parameters of unit 1 are accessible (254). Pressing the 'screen' key then allows accessing unit 2 or second pump-unit, and thus parameters of unit 2. Several procedures may then be activated (260) with respect to unit 2, such as configuration, programming, start-up or parameters display (262). Another pressing of the 'screen' key (264) then allows accessing back to unit 1 parameters. When accessing unit 2, infusion with unit 1 would proceed normally. One will appreciate that the system thus behaves as two independent infusion pump systems sharing common resources (controller, its keyboard and its screen).

It is to be noted that accessing the other unit is not authorized when a first unit has entered certain procedures such as configuration, programming or air draining.

An example of procedure is given in FIGS. 10a-10d. The illustrated example is with programming procedure, but the other procedures that the controller according to the invention can activate follow the same pattern.

Figure 10B:
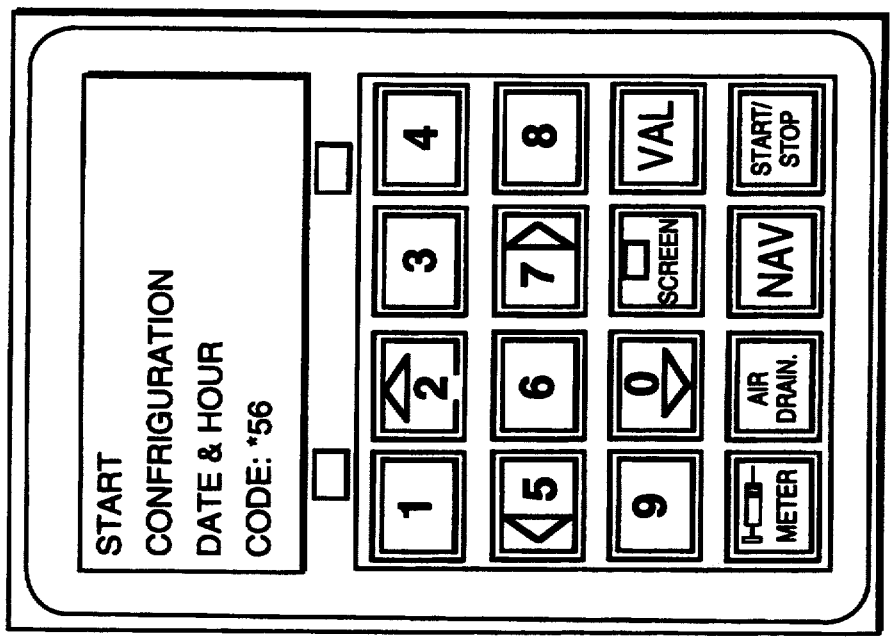
Figure 10A:
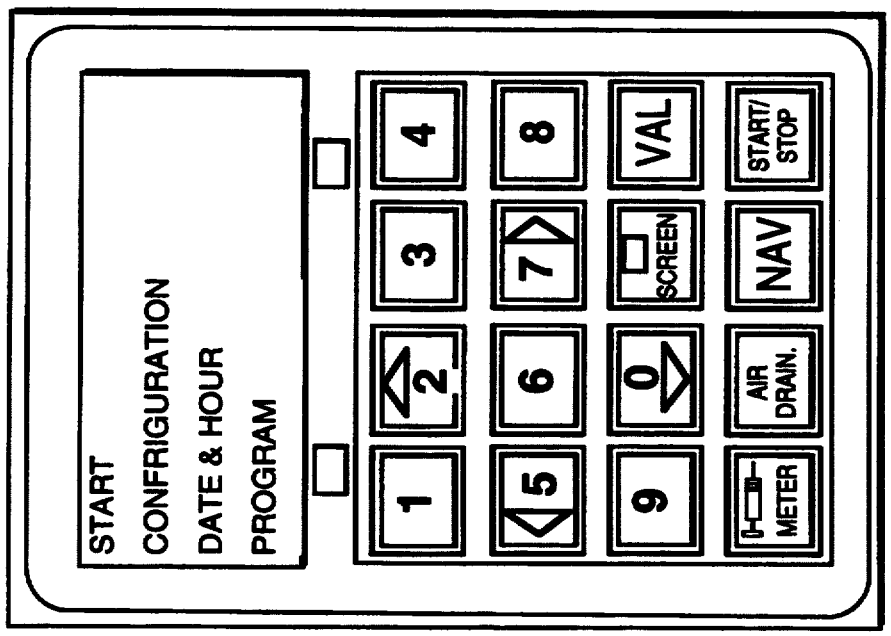

At the beginning, powered-on controller shows like what is illustrated in FIG. 10a, i.e. the four possible procedures are displayed on the screen: START, CONFIGURATION, DATE AND TIME and PROGRAM. Using the top key (key '2') of the keyboard, or the bottom key (key '0'), it is possible to choose one of the displayed procedures. Supposing the PROGRAM procedure is chosen, this choice gets validated by pressing the key 'VAL' on the keyboard. The latter validation triggers a display screen as seen FIG. 10b where the fourth line becomes CODE. Access code, here 56, is input at the keyboard and validated by the key 'VAL'.

Infusion parameters then appear on the screen: 'Intensity', 'Capacity''Duration''KVO' in front of which the doctor or specialist inputs the necessary quantities. Thus, as seen in FIG. 10c, intensity is set to 50 ml/h, capacity is set to 300 ml, duration to 3 hours. KVO (Keep Vein Open) set to 1.5 ml/h means that when there is no actual infusion, for example in the INTERMITTENT configuration mode a minimum flow of 1.5 ml/h is kept in the infusion tube.

Figure 10D:
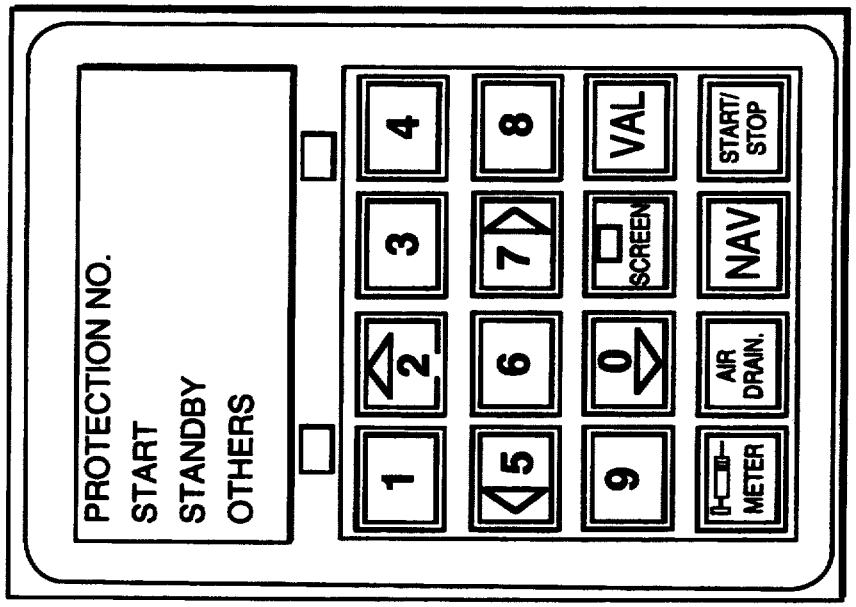
Figure 10C:
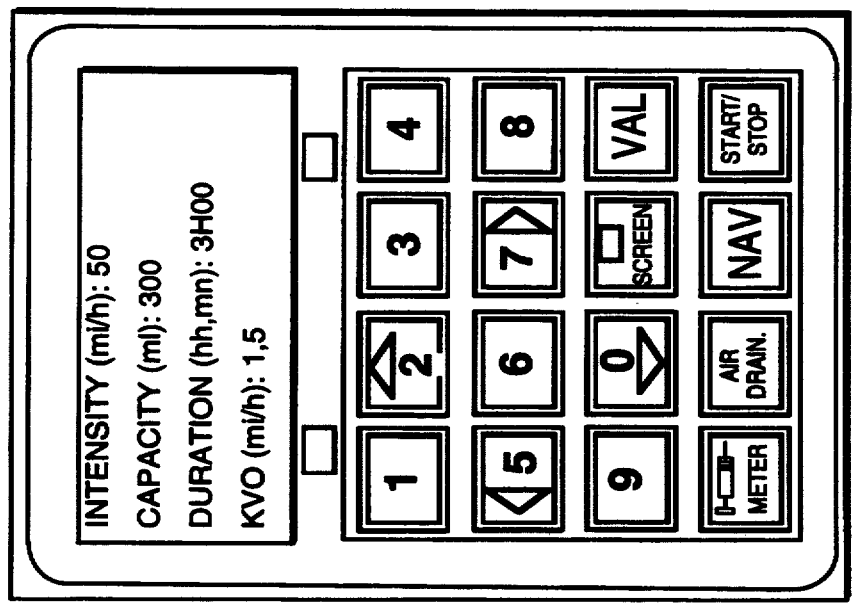

After validation of the infusion parameters, a choice is made between four alternatives, as seen FIG. 10d. They are START to start-up the infusion, STANDBY which puts the pump in standby, PROTECTION or OTHERS. The choice PROTECTION No corresponds to different levels at which the patient is authorized to perform certain operations by himself. Thus level 0 could be when the patient cannot perform any operation, the level 1 when he can change the cassette by himself, etc . . . .

As seen in FIGS. 10a to 10d, certain keys of the keyboard are reserved and specialized. Thus the key 'screen' performs as switch to display infusion parameters of unit 2 when the system is previously displaying parameters of unit 1. The key 'DRAIN' allows the draining of any air from the infusion tube. The key METER is used directly by the patient in the PCA mode to perform regular injection of analgesic substance. It is obvious that other functions may be associated with these keys, or that other keys can be associated with specific functions not represented on FIGS. 10a-10d.

Although in the preferred embodiment of the invention, command of the pump-unit motor is ensured thru physical connections, it is possible to conceive a remote control. In the latter case, the controller will feature a signal emitter and the pump-unit a receiver but also a battery for providing the motor with power that it does not receive anymore from the controller due to the lack of physical connection.

What is claimed is:

1. A programmable and portable infusion pump system for injecting a medicinal substance into the body of a patient in accordance with a first predetermined infusion process, the system comprising;

a programmable controller having a microprocessor, a keyboard, a screen adapted to display the first predetermined infusion process, and means connecting said keyboard to said microprocessor to enable programming of said microprocessor in accordance with the displayed first predetermined infusion process, a first medicinal substance injection unit, means detachably mounting said first injection unit to said controller, said first injection unit having a first supply chamber within adapted to contain a first medicinal substance, a first motor, and a first pump connected to be driven by said first motor, a first infusion tube connected to said first supply chamber and adapted to be connected to the body of the patient, means within said first injection unit connecting said first pump to said first infusion tube for injecting the first medicinal substance from said first supply chamber into said first infusion tube, and means connecting said first motor to be controlled by said microprocessor in accordance with the first predetermined infusion process.

2. The system of claim 1, including a second infusion unit detachably connected to said controller for injecting a second medicinal substance into the body of a patient in accordance with a second predetermined infusion process, said screen displaying the second predetermined infusion process, and said keyboard enable programming of said microprocessor in accordance with the second predetermined infusion process, said second infusion unit having;
- a second supply chamber adapted to contain a second medicinal substance, a second motor,
- a second pump connected to be driven by said second motor,
- a second infusion tube connected to said second supply chamber and adapted to be connected to the body of the patient,
- means connecting said second pump to said second infusion tube for injecting the second medicinal substance from said second supply chamber into said second infusion tube, and
- said means connecting said second motor to be controlled by said microprocessor in accordance with the second predetermined infusion process.

3. The system of claim 2 including;
- a first and a second elongated cable electrically connecting said first and second infusion units to said controller to provide said control of said first and second motors by said microprocessor when said first and second infusion units are detached from said controller.

4. The system of claim 1 including memory means in said controller, said memory means operating to store a history of the injecting of the first medicinal substance into the body of a patient in accordance with the first predetermined infusion process.

5. The system of claim 2 including memory means in said controller, said memory means operating to store a history of the injecting of the first and second medicinal substances into the body of a patient in accordance with the first and second predetermined infusion processes.

6. The system of claim 1 including;
- a first pressure sensor in said first infusion tube, and
- means connecting said first pressure sensor to said controller.

7. The system of claim 2 including;
- a first and a second pressure sensor in said first and second infusion tubes, and
- means connecting said first and second pressure sensors to said controller.

8. The system of claim 1 including;
- a plurality of physiological sensors adapted to be associated with the patient, and
- means connecting said sensors to said controller to additionally control said first motor.

9. The system of claim 2 including;
- a plurality of physiological sensors adapted to be associated with the patient, and
- means connecting said sensors to said controller to additionally control said first and second motors.

10. The system of claim 1 including;
- a bar code reading system connected to said controller to enable said controller to be programmed using an optical pen.

11. The system of claim 2 including;
- a bar code reading system connected to said controller to enable said controller to be programmed using an optical pen.

12. The system of claim 1 including;
- an electronic card reading system connected to said controller to enable said controller to be programmed using an electronic card.

13. The system of claim 2 including;
- an electronic card reading system connected to said controller to enable said controller to be programmed using an electronic card.

14. The system of claim 1 including;
- a modem connected to said controller to enable said controller to be programmed by connection to a telephone network.

15. The system of claim 2 including;
- a modem connected to said controller to enable said controller to be programmed by connection to a telephone network.

16. The system of claim 1 wherein said first supply chamber is disposable, and including;
- a removable elastic clipping mechanism connecting said first supply chamber to said first pump.

17. The system of claim 2 wherein said first and second supply chambers are disposable, and including;
- first and second removable elastic clipping mechanisms connecting said first and second supply chambers to said first and second pumps.

18. The system of claim 1 including;
- memory means in said controller storing patient information relative to an infusion, and
- means including said memory means for modifying control of said first motor.

19. A method enabling an individual to administer a first medicinal substance to the body of the individual in an unsupervised manner, comprising the steps of;
- providing visual means displaying first microprocessor programming parameters that define a first predetermined infusion process by which the first medicinal substance may be administered to the individual,
- providing a programmable controller unit having a microprocessor and a keyboard by which the individual may manually program said microprocessor in accordance with said first microprocessor programming parameters,
- providing a first medicinal substance injection unit that is detachably connected to said controller unit by means of an elongated electrical cable,
- providing a first supply chamber within said first injection unit adapted to contain a the first medicinal substance,
- providing a first motor within said first injection unit,
- providing a first pump within said first injection unit connected to be driven by said first motor,
- providing a first infusion tube having a first end connected to said first supply chamber and having a second end adapted to be connected to the body of the individual,
- connecting said first pump to said first infusion tube for injecting the first medicinal substance from said first supply chamber into said first infusion tube, and
- providing means including said cable connecting said first motor to be controlled by said microprocessor in accordance with the first microprocessor programming parameters,
- displaying second microprocessor programming parameters at said visual means that define a second predetermined infusion process for the second medicinal substance to the individual,
- manually programming said microprocessor in accordance with said second microprocessor programming parameters,
- providing a second medicinal substance injection unit that is detachably connected to said controller unit by means of a second elongated electrical cable, providing a second supply chamber within said second injection unit adapted to contain the second medicinal substance, providing a second motor within said second injection unit, providing a second pump within said second injection unit connected to be driven by said second motor, providing a second infusion tube having a first end connected to said second supply chamber and having a second end adapted to be connected to the body of the individual, connecting said second pump to said second infusion tube for injecting the second medicinal substance from said second supply chamber into said second infusion tube, and providing means including said second cable connecting said second motor to be controlled by said microprocessor in accordance with the second microprocessor programming parameters.

20. The method of claim 19 including the step of;
providing said first supply chamber as a disposable supply chamber.

21. The method of claim 19 including the step of;
providing said second supply chamber as a disposable supply chamber.

22. The method of claim 19 including the step of;
providing means enabling programming of said microprocessor in accordance with said first microprocessor programming parameters by the use of a means selected from the group bar code reader, card reader, modem, and personal computer.

23. The method of claim 19 including the step of;
providing means enabling programming of said microprocessor in accordance with said first and second microprocessor programming parameters by the use of a means selected from the group bar code reader, card reader, modem, and personal computer.

24. The method of claim 19 including the step of;
providing a real time clock within said microprocessor.

25. The method of claim 24 including the step of;
providing a pressure sensor within said first infusion tube and connected to said microprocessor.

26. The method of claim 25 including the step of;
providing an air bubble detector within said first infusion tube and connected to said microprocessor.

27. The method of claim 19 including the step of;
providing an access code enabling use of said keyboard by the individual to obtain access to said microprocessor prior to the individual programming said microprocessor in accordance with said first microprocessor programming parameters.

* * * * *